United States Patent
Nielsen et al.

(10) Patent No.: US 10,451,603 B2
(45) Date of Patent: Oct. 22, 2019

(54) CONTAMINANT SENSOR FOR DETECTING MAGNETIZABLE CONTAMINANTS IN LUBRICANT FLOW

(71) Applicant: Vestas Wind Systems A/S, Aarhus N. (DK)

(72) Inventors: Thomas Korsgaard Nielsen, Vejle (DK); Jan Hove Pedersen, Risskov (DK)

(73) Assignee: Vestas Wind Systems A/S, Aarhus N. (DK)

( * ) Notice: Subject to any disclaimer, the term of this patent is extended or adjusted under 35 U.S.C. 154(b) by 284 days.

(21) Appl. No.: 15/516,111

(22) PCT Filed: Nov. 16, 2015

(86) PCT No.: PCT/DK2015/050350
§ 371 (c)(1),
(2) Date: Mar. 31, 2017

(87) PCT Pub. No.: WO2016/078665
PCT Pub. Date: May 26, 2016

(65) Prior Publication Data
US 2017/0254794 A1    Sep. 7, 2017

(30) Foreign Application Priority Data

Nov. 21, 2014    (DK) .................................. 2014 70729

(51) Int. Cl.
*G01N 33/28*    (2006.01)
*G01N 15/06*    (2006.01)
(Continued)

(52) U.S. Cl.
CPC ......... *G01N 33/2858* (2013.01); *F03D 15/00* (2016.05); *F03D 80/70* (2016.05);
(Continued)

(58) Field of Classification Search
CPC ............................................................ B03C 1/284; B03C 1/288; B03C 1/30; B03C 2201/18; F03D 15/00; F03D 80/70;
(Continued)

(56) References Cited

U.S. PATENT DOCUMENTS 4,219,805 A * 8/1980 Magee ..................... F16N 29/04
324/204
4,323,843 A    4/1982 Batham
(Continued)

FOREIGN PATENT DOCUMENTS

EP    0116468 A1    8/1984
GB    2029580 A    3/1980
(Continued)

OTHER PUBLICATIONS

European Patent Office, Examination Report in EP15800713.8, dated Mar. 22, 2018.
(Continued)

*Primary Examiner* — John Fitzgerald
*Assistant Examiner* — Truong D Phan
(74) *Attorney, Agent, or Firm* — Wood Herron & Evans LLP

(57) ABSTRACT

A contaminant sensor (1) for detecting magnetizable contaminants (7) present in a lubricant flow is disclosed. A permanent magnet (3) is arranged movably inside a sensor housing (2). A sensor element (6, 11, 13), e.g. in the form of a distance sensor (6) or a pressure sensor (11), is arranged to detect a displacement of the permanent magnet (3) inside the sensor housing (2), and an indicator is arranged to generate an alert signal when a displacement and/or a rate of change of displacement of the permanent magnet (3) inside the sensor housing (2) exceeds a predefined threshold value. The permanent magnet (3) is arranged to move inside the sensor
(Continued)

housing (2) in response to magnetizable contaminants (7) collected on an outer surface of the sensor housing (2).

12 Claims, 11 Drawing Sheets

(51) Int. Cl.
*F03D 15/00* (2016.01)
*F03D 80/70* (2016.01)
*F16N 29/00* (2006.01)
*G01L 1/04* (2006.01)
*B03C 1/03* (2006.01)
*B03C 1/28* (2006.01)
*B03C 1/30* (2006.01)

(52) U.S. Cl.
CPC ................ *F16N 29/00* (2013.01); *G01L 1/04* (2013.01); *G01N 15/06* (2013.01); *G01N 33/2888* (2013.01); *F05B 2260/98* (2013.01)

(58) Field of Classification Search
CPC .. F05B 2260/98; F16N 2250/32; F16N 29/00; G01L 1/04; G01N 15/06; G01N 15/0656; G01N 33/2858; G01N 33/2888; G01N 27/72; G01N 27/74; B60L 13/06; B60L 2200/26; G01B 7/003; G01B 7/30; G01B 7/14; G01B 7/312; G01F 23/2963; G01R 33/09; F15B 15/2815; G01P 3/487; G01P 3/443; G01D 11/245; G01D 5/485; G01D 5/145; G01D 5/147
USPC ............................. 73/61.71, 53.05; 324/204, 324/207.11–207.16, 207.21, 207.2–207.25
See application file for complete search history.

(56) References Cited

U.S. PATENT DOCUMENTS

| | | | |
|---|---|---|---|
| 4,495,799 A | 1/1985 | Fisher et al. | |
| 4,651,091 A * | 3/1987 | Chambers | G01N 3/56 324/204 |
| 4,692,698 A | 9/1987 | Lewis | |
| 5,214,377 A * | 5/1993 | Maurice | G01N 33/2858 250/225 |
| 5,262,732 A | 11/1993 | Dickert et al. | |
| 5,341,126 A * | 8/1994 | Boykin | G08B 21/0247 324/234 |
| 5,614,830 A * | 3/1997 | Dickert | G01N 15/0656 210/695 |
| 5,674,401 A * | 10/1997 | Dickert | G01N 15/0656 210/695 |
| 5,675,249 A * | 10/1997 | LaClair | G01N 1/34 250/227.17 |
| 5,708,198 A * | 1/1998 | Fitch | G01N 15/0656 73/61.42 |
| 6,633,157 B1 * | 10/2003 | Yamaki | F01L 9/04 123/90.11 |
| 2005/0231193 A1 * | 10/2005 | Yamamoto | G01D 5/145 324/207.2 |
| 2007/0188161 A1 * | 8/2007 | Asa | G01D 5/145 324/207.11 |
| 2008/0143525 A1 * | 6/2008 | Woodbury | G01D 5/147 340/547 |
| 2010/0089131 A1 * | 4/2010 | Niksa | G01N 27/126 73/53.05 |
| 2011/0192224 A1 | 8/2011 | Vonsild et al. | |
| 2013/0332045 A1 | 12/2013 | Uluyol et al. | |

FOREIGN PATENT DOCUMENTS

| | | |
|---|---|---|
| WO | 8502014 A1 | 5/1985 |
| WO | 2007088015 A1 | 8/2007 |
| WO | 2014005673 A1 | 1/2014 |
| WO | 2014019587 A1 | 2/2014 |

OTHER PUBLICATIONS

European Patent and Trademark Office, International Search Report and Written Opinion in PCT Application Serial No. PCT/DK2015/050350, dated Feb. 17, 2016.

Danish Patent and Trademark Office, Search Report in PA 2014 70729, dated Jun. 18, 2015.

* cited by examiner

CONTAMINANT SENSOR FOR DETECTING MAGNETIZABLE CONTAMINANTS IN LUBRICANT FLOW

FIELD OF THE INVENTION

The present invention relates to a contaminant sensor for detecting magnetizable contaminants in a lubricant flow. The contaminant sensor of the invention allows the contaminants to be detected in an easy and simple manner. The invention further relates to a lubrication system having the contaminant sensor arranged therein, and a wind turbine comprising such a lubrication system.

BACKGROUND OF THE INVENTION

In lubrication systems, where a lubricant is circulated in order to provide lubrication, e.g. for a moving part, it is undesirable that contaminants, e.g. in the form of debris, are present in the lubricant, since this may potentially lead to damage of the moving part. More important, contaminants may, e.g., originate from the moving part being lubricated, and as a consequence of the movements of the moving part, and in this case the presence of contaminants in the lubricant is an indication that a moving part has already suffered some damage, e.g. in the form of white structure flacking or tooth fracture. In the case that the moving part is made from a magnetizable material, such as iron, nickel, cobalt, or alloys containing iron, nickel or cobalt, the contaminants will also be magnetizable. As an alternative, the magnetizable material may be rare earth metal.

Thus, it is desirable to be able to detect the presence of contaminants, such as magnetizable contaminants, in a lubricant, in order to detect if the moving part being lubricated has suffered some damage, and in order to prevent that the moving part is damaged further. This has previously been obtained by means of magnetic sensors.

US 2013/0332045 A1 discloses a system and a method for detecting a spall in an engine by means of an oil debris sensor. A processor may be configured to increment a counter when the oil debris sensor detects a particle over a predetermined size, and to increment the counter when a mass of a plurality of particles under the predetermined size exceeds a predetermined mass threshold. The processor may analyse data from the sensor to determine when a change in an electromagnetic field has occurred, indicating a debris article.

WO 2007/088015 A1 discloses an apparatus, in particular an inductive particle counter, for detecting particles in a fluid flow and associated cooling and/or lubricating system. The apparatus has at least one field coil for generating a magnetic field, which covers at least sections of the fluid flow, and a sensor coil which can be connected to an evaluation device which can be used to detect the presence of a particle in the fluid flow from the signal induced in the sensor coil.

The systems and methods disclosed in US 2013/0332045 A1 and WO 2007/088015 A1 rely on relatively complicated approaches for detecting the presence of contaminants in a lubricant flow.

DESCRIPTION OF THE INVENTION

It is an object of embodiments of the invention to provide a contaminant sensor which is capable of detecting the presence of magnetizable contaminants in a lubricant flow in an easy and cost effective manner.

It is a further object of embodiments of the invention to provide a contaminant sensor which allows the contaminants to be collected and removed from the lubricant, e.g. for further inspection.

According to a first aspect the invention provides a contaminant sensor for detecting magnetizable contaminants present in a lubricant flow, the contaminant sensor comprising:

a sensor housing,
a permanent magnet arranged movably inside the sensor housing,
a resilient member operationally coupled to the permanent magnet,
a sensor element arranged to detect a displacement of the permanent magnet inside the sensor housing,
an indicator arranged to generate an alert signal when a displacement and/or a rate of change of displacement of the permanent magnet inside the sensor housing exceeds a predefined threshold value, wherein the permanent magnet is arranged to move inside the sensor housing in response to magnetizable contaminants collected on an outer surface of the sensor housing.

According to the first aspect, the invention relates to a contaminant sensor for detecting magnetizable contaminants present in a lubricant flow. In the present context the term 'contaminants' should be interpreted to mean material, e.g. in the form of particles, which is not supposed to be present in the lubricant, and which may potentially originate from the parts being lubricated by means of the lubricant. In the present context the term 'magnetizable contaminants' should be interpreted to mean contaminants which are made from a material which can be magnetised, i.e. which can be attracted by means of a magnetic force. The material of the magnetizable contaminants could, e.g., be a ferrous material, such as iron or an iron-containing alloy, or another kind of magnetizable material, such as nickel or a nickel-containing alloy, or cobalt or a cobalt-containing alloy. As another alternative, the magnetizable material may be or comprise a rare earth metal. In any event, the magnetizable contaminants will be attracted to a magnet arranged in the vicinity of the magnetizable contaminants.

The contaminant sensor comprises a sensor housing. In the present context the term 'sensor housing' should be interpreted to mean a substantially closed structure defining an interior part which is delimited from the exterior of the sensor by means of one or more wall parts.

The contaminant sensor further comprises a permanent magnet arranged movably inside the sensor housing. This should be interpreted to mean that the permanent magnet is not fixed to the sensor housing, but is allowed to move relative to the sensor housing, even if such movements may be very small. This will be described in further detail below. Thus, the permanent magnet can be displaced relative to the sensor housing.

Furthermore, the contaminant sensor comprises a resilient member operationally coupled to the permanent magnet. In the present context the term 'resilient member' should be interpreted to mean a member or a part which can be temporarily compressed, stretched, bent or deformed in response to a force being exerted on the member, and which is capable of restoring an original shape and size when the force is no longer exerted on the member.

Since the resilient member is operationally coupled to the permanent magnet, movements of the magnet inside the sensor housing may result in a force being exerted on the resilient member, and may therefore result in the resilient member being compressed, stretched, bent or deformed.

The contaminant sensor further comprises a sensor element arranged to detect a displacement of the permanent magnet inside the sensor housing. The sensor element may be arranged to detect the displacement directly. Alternatively, the sensor element may be arranged to detect another parameter which changes as a result of the displacement. It should be noted that the displacement of the permanent magnet inside the sensor housing may be very small, but the very small displacement may result in a detectable change in a measured parameter, such as a stress, a strain, a pressure or a force introduced in an element arranged adjacent to the permanent magnet. This will be described in further detail below.

The permanent magnet is arranged to move inside the sensor housing in response to magnetizable contaminants being collected on an outer surface of the sensor housing. Since the contaminants are magnetizable they are attracted to the permanent magnet of the contaminant sensor. The magnetizable contaminants will not be able to reach the permanent magnet, since the permanent magnet is arranged inside sensor housing, and the magnetizable contaminants are present in the lubricant flow, i.e. outside the sensor housing.

In the present context the term 'outer surface of the sensor housing' should be interpreted to cover a surface of a wall part of the sensor housing, as well as a surface of a separate part arranged outside the sensor housing. Furthermore, the outer surface may not necessary be a solid surface, but could also be a grid structure or the like. In any event, contaminants collected at the outer surface will not be able to reach the permanent magnet, as described above.

However, due to the magnetic attraction between the permanent magnet and the magnetizable contaminants, the magnetizable contaminants will be collected on an outer surface of the sensor housing, and will be retained there by means of the magnetic force provided by the permanent magnet. Furthermore, the magnetic attraction will cause the permanent magnet to move inside the sensor housing, in a direction towards the region where the magnetizable contaminants are collected. The amount of collected material determines how much the permanent magnet moves, i.e. the displacement of the permanent magnet reflects the amount of collected material. Furthermore, the amount of magnetizable contaminants which have been collected during a given time period will normally be representative for the level of magnetizable contaminants present in the lubricant flow. Accordingly, the displacement of the permanent magnet provides a suitable measure for the level of magnetizable contaminants being present in the lubricant flow.

The contaminant sensor further comprises an indicator arranged to generate an alert signal when a displacement and/or a rate of change of displacement of the permanent magnet inside the sensor housing exceeds a predefined threshold value.

When the displacement of the permanent magnet inside the sensor housing reaches a predefined threshold value, this indicates that a predefined amount of magnetizable contaminants has been collected on the outer surface of the sensor housing. If the predefined threshold value is reached before a specified time period has elapsed, this may be an indication that the level of magnetizable contaminants present in the lubricant flow is too high, and that inspection of the lubrication system may be required in order to prevent further damage to the parts being lubricated by means of the lubrication system. Therefore the indicator may generate an alert in this case. As an alternative to detecting the amount of contaminants collected during a specified time period, the amount of contaminants collected during production of a specified amount of power or energy, or relative to any other suitable parameter.

When the rate of change of displacement of the permanent magnet exceeds a predefined threshold value, this is an indication that magnetizable contaminants are collected on the outer surface of the sensor housing faster than an acceptable rate. This may indicate that the level of magnetizable contaminants present in the lubricant flow has increased suddenly. This may, e.g., be an indication that a moving part of the system being lubricated has been damaged, and that inspection of the system may therefore be required. In this case it is an advantage that an alert signal is generated in response to the increase in rate of change of the displacement of the permanent magnet, instead of awaiting that a predefined displacement is reached, because the possible damage to the moving part may thereby be detected and corrected earlier, and serious damage may thereby be prevented.

Thus, by means of the contaminant sensor of the invention the presence of magnetizable contaminants in a lubricant flow can be detected in an easy and reliable manner. Furthermore, the contaminant sensor can be provided in a cost effective manner, since it does not rely on complicated or sensible technology or components.

The resilient member may be or comprises a spring element and/or a bellow. The spring element may, e.g., be a compressible spring, a torsion spring, a disc spring or a leaf spring. The bellow may have an incompressible medium, such as a liquid, arranged inside thereof, or the bellow may be arranged in a container, e.g. in the form of the sensor housing, containing an incompressible medium. This will be described in further detail below.

Alternatively or additionally, the resilient member may be or comprise a deformable or bendable part, such as a part made from a rubber material, and/or a part in which strain or stress is introduced in response to a force being exerted thereon.

The sensor element may be or comprise a distance sensor arranged to measure a distance between the distance sensor and the permanent magnet or a member attached to the permanent magnet. Assuming that the distance sensor is arranged in a fixed position relative to the sensor housing, a displacement of the permanent magnet relative to the sensor housing will also result in a displacement of the permanent magnet relative to the distance sensor. Therefore a change in a distance between the permanent magnet, or a member attached to the permanent magnet, and the distance sensor corresponds to the displacement of the permanent magnet. Thus, according to this embodiment the displacement of the permanent magnet is measured directly.

When the permanent magnet moves as a result of the magnetizable contaminants being collected on the outer surface of the sensor housing, the permanent magnet may be moved in a direction towards the distance sensor or in a direction away from the distance sensor. In the case that the permanent magnet is moved in a direction towards the distance sensor, the displacement of the permanent magnet may reach the predefined threshold value when the distance between the permanent magnet, or a member attached to the permanent magnet, and the distance sensor decreases below a specified lower limit.

Similarly, in the case that the permanent magnet is moved in a direction away from the distance sensor, the displacement of the permanent magnet may reach the predefined threshold value when the distance between the permanent magnet, or a member attached to the permanent magnet, and the distance sensor increases above a specified upper limit.

The resilient member may be or comprise a bellow attached to the permanent magnet, and the sensor element may be or comprise a pressure sensor arranged to measure a pressure inside and/or outside the bellow.

Since the bellow is attached to the permanent magnet, movements of the permanent magnet will result in a force being exerted on the bellow, which will attempt to compress or stretch the bellow. In the case that the bellow has an incompressible medium, such as a liquid, arranged inside the bellow, it will not be possible to compress or stretch the bellow. Instead the force exerted on the bellow, by the permanent magnet, results in a change in the pressure inside the bellow. Accordingly, the pressure inside the bellow provides a measure for the force exerted on the bellow by the movement of the permanent magnet. It should be noted that, according to this embodiment, the actual displacement of the permanent magnet will be very small, and that the movements of the permanent magnet, due to the collected magnetizable contaminants, are transformed into a force being exerted on the bellow, and thereby a change in the pressure inside the bellow.

According to an alternative embodiment, the bellow may have a compressible medium, such as a gas arranged inside the bellow, but the bellow may be arranged in an incompressible medium, such as a liquid. In this case the pressure of the liquid will change in response to the bellow being compressed or stretched, and thereby the pressure outside the bellow, i.e. the pressure of the liquid, will be a suitable measure for the force exerted on the bellow by means of the moving permanent magnet. Accordingly, the pressure outside the bellow, in this case, provides a suitable measure for the displacement of the permanent magnet.

The sensor element may be or comprise a force sensor arranged to measure a force exerted by the permanent magnet. According to this embodiment, the sensor element may, e.g., be of a kind which is adapted to measure strain or stress introduced in an element or a part as a result of the force exerted by the permanent magnet when it moves due to the magnetic attraction between the permanent magnet and the contaminants collected on the outer surface of the sensor housing. For instance, the sensor element may comprise a strain gauge or a piezo resistive element.

The permanent magnet may be movable against a force provided by the resilient member in response to magnetizable contaminants collected on the outer surface of the sensor housing. According to this embodiment, the resilient member is arranged to bias the permanent magnet in a direction away from the region of the sensor housing where the contaminants are collected. This ensures that the permanent magnet is moved gradually towards this region of the sensor housing, as the contaminants are collected.

The sensor element may be at least partly arranged inside the sensor housing. Thereby the sensor element is protected against the lubricant in which the contaminant sensor is arranged.

According to a second aspect the invention provides a lubrication system for lubricating a wind turbine component, the lubrication system having a contaminant sensor according to the first aspect of the invention detachably mounted therein.

According to this aspect the contaminant sensor is used for detecting the presence of contaminants in lubricant used for lubricating a wind turbine component. Thereby further damage to the wind turbine component can be prevented, as described above. Since the contaminant sensor is detachably mounted in the lubrication system, the contaminant sensor can be removed from the lubrication system, e.g. for inspection, repair, maintenance or replacement.

The wind turbine component may be or form part of a drive train. For instance, the wind turbine component could be a large transmission gear of a wind turbine. As an alternative, the wind turbine component may be or form part of a yaw system, a pitch system, or a bearing system of a wind turbine.

The contaminant sensor may be arranged to retain contaminants collected on an outer surface of the sensor housing, the collected contaminants thereby being removable from the lubrication system along with the detachable contaminant sensor. According to this embodiment, contaminants which are collected on the outer surface of the sensor housing during use of the contaminant sensor remain attached to the outer surface of the sensor housing. When the contaminant sensor is removed from the lubrication system, e.g. in response to an alert signal generated by the indicator, or as a part of a regular service inspection, the collected contaminants are removed from the lubrication system along with the contaminant sensor. This allows the collected contaminants to be inspected and/or analysed, e.g. in order to determine the origin of the contaminants.

According to a third aspect the invention provides a wind turbine comprising a lubrication system according to the second aspect of the invention.

It should be noted that a skilled person would readily recognise that any feature described in combination with the first aspect of the invention could also be combined with the second or third aspects of the invention, that any feature described in combination with the second aspect of the invention could also be combined with the first and third aspects of the invention, and that any feature described in combination with the third aspect of the invention could also be combined with the first and second aspects of the invention. The remarks set forth above are therefore equally applicable here.

BRIEF DESCRIPTION OF THE DRAWINGS

The invention will now be described in further detail with reference to the accompanying drawings in which.

DETAILED DESCRIPTION OF THE DRAWINGS

Figure 1A:
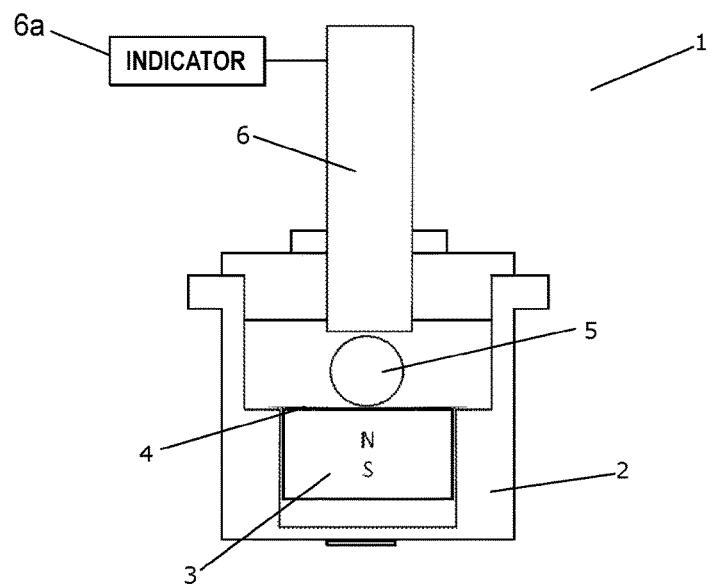
FIGS. 1a-1c are cross sectional views of a contaminant sensor according to a first embodiment of the invention.
Figure 1B:
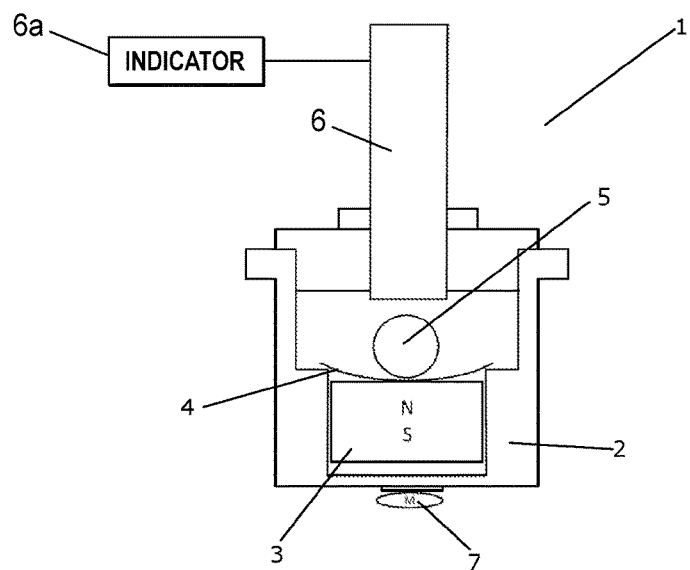
Figure 1C:
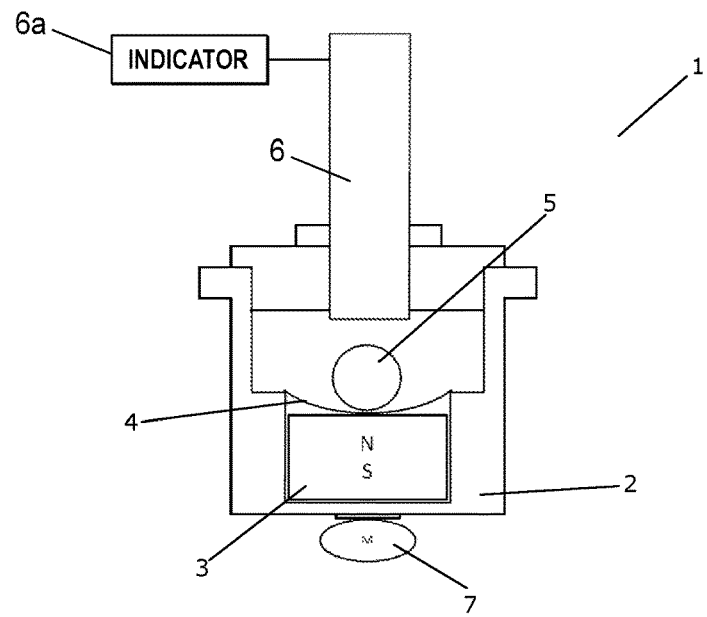

FIGS. 1a-1c are cross sectional views of a contaminant sensor 1 according to a first embodiment of the invention. In FIG. 1a the contaminant sensor 1 is not activated, in FIG. 1b the contaminant sensor 1 is partly activated, and in FIG. 1c the contaminant sensor 1 is fully activated.

The contaminant sensor comprises a sensor housing 2 having a permanent magnet 3 arranged movably therein. A resilient member, in the form of a flexible disc 4 (or a leaf spring) is coupled to the permanent magnet 3 and to a distance member 5. The distance member 5 is thereby coupled to the permanent magnet 3, via the flexible disc 4, and the position of the distance member 5 inside the sensor housing 2 is therefore determined by the position of the permanent magnet 3.

A sensor element, in the form of a distance sensor 6, is arranged partly inside the sensor housing 2, and is arranged to detect a distance between an end part of the distance sensor 6 and the distance member 5. Since this distance is defined by the position of the distance member 5 inside the sensor housing 2, the distance is a measure for a displacement of the permanent magnet 3.

The contaminant sensor 1 can be arranged in a lubricant flow in such a manner that the part of the sensor housing 2, which is arranged opposite to the position of the distance sensor 6, is arranged in contact with the lubricant. Thereby magnetizable contaminants present in the lubricant flow will be attracted towards the contaminant sensor 1 and collected on an outer surface of the sensor housing 2, due to the magnetic field generated by the permanent magnet 3. Furthermore, magnetizable contaminants being attracted towards the contaminant sensor 1 in this manner will remain attached to the sensor housing 2, due to the magnetic field. This will be described further below.

In FIG. 1a no contaminants have been attracted towards the contaminant sensor 1, and therefore no contaminants have been collected on the outer surface of the sensor housing 2. As a consequence, the permanent magnet 3 is arranged as close to the distance sensor 6 as possible, and the flexible disc 4 is in a relaxed state.

In FIG. 1b some contaminants 7 have been collected at the outer surface of the sensor housing 2. This has caused the permanent magnet 3 to be attracted by the collected contaminants 7, thereby moving the permanent magnet 3 towards the collected contaminants 7, against a biasing force provided by the flexible disc 4. Accordingly, the distance member 5 has been moved away from the distance sensor 6, i.e. the distance measured by the distance sensor 6 has increased.

In FIG. 1c a larger amount of contaminants 7 has been collected at the outer surface of the sensor housing 2. This has caused the permanent magnet 3 to be moved closer to the collected contaminants 7. Thereby the distance member 5 has been moved further away from the distance sensor 6, i.e. the distance measured by the distance sensor 6 has been further increased. This has caused the distance measured by the distance sensor 6 to increase above a predefined threshold value, indicating that the amount of collected contaminants 7 is above a given threshold value. If a certain amount of contaminants 7 is collected within a certain amount of time, this is an indication that a high concentration of magnetizable contaminants 7 is present in the lubricant flow. This may be due to damage or wear on moving parts being lubricated by means of the lubrication system, and therefore an indicator 6a generates an alert in this case, e.g. in order to inform an operator that an inspection of the lubrication system is required.

When the permanent magnet 3 is moved as described above, it moves against the biasing force provided by the flexible disc 4. This ensures that the permanent magnet 3 moves gradually, and that the displacement of the permanent magnet 3 provides a suitable measure for the amount of magnetizable contaminants 7 which has been collected at the outer surface of the sensor housing 2.

Figure 2A:
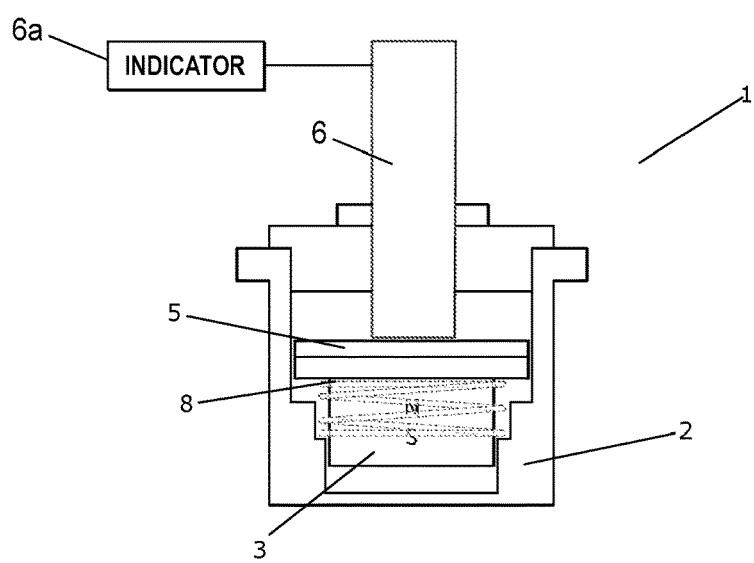
FIGS. 2a-2c are cross sectional views of a contaminant sensor according to a second embodiment of the invention.
Figure 2B:
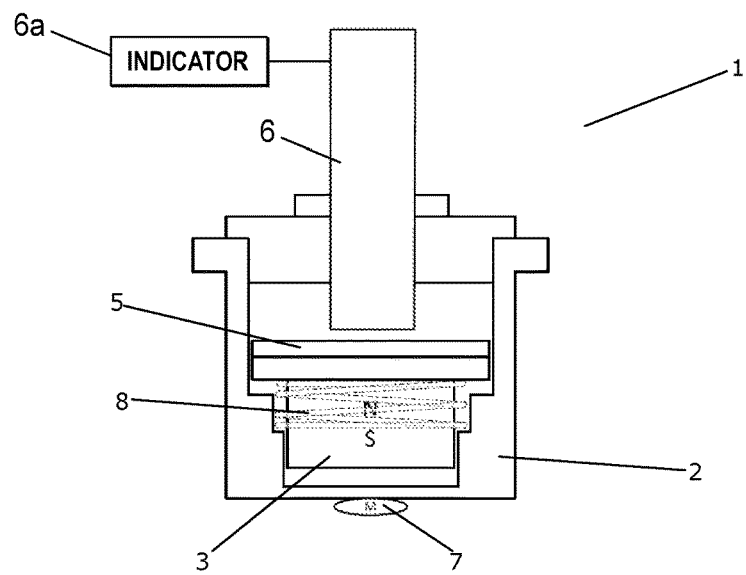
Figure 2C:
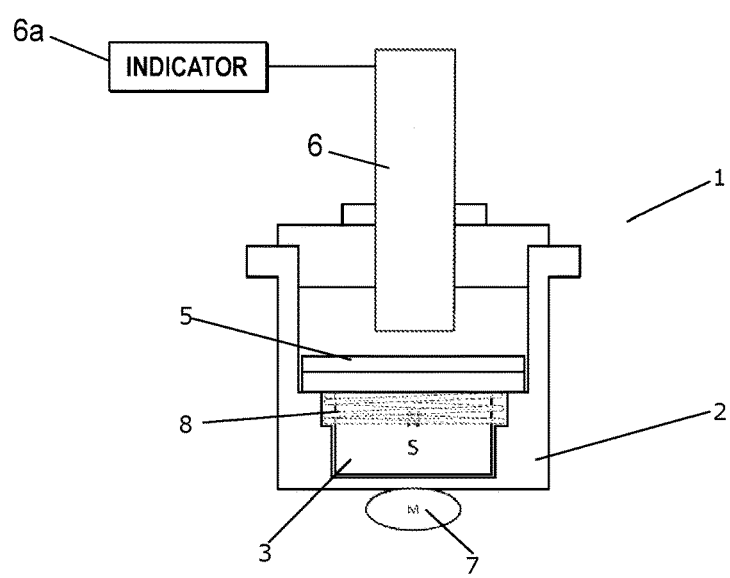

FIGS. 2a-2c are cross sectional views of a contaminant sensor 1 according to a second embodiment of the invention. In FIG. 2a the contaminant sensor 1 is not activated, in FIG. 2b the contaminant sensor 1 is partly activated, and in FIG. 2c the contaminant sensor 1 is fully activated.

The contaminant sensor 1 of FIGS. 2a-2c is very similar to the contaminant sensor 1 of FIGS. 1a-1c, and it will therefore not be described in detail here.

As compared to the embodiment illustrated in FIGS. 1a-1c, in the contaminant sensor 1 of FIGS. 2a-2c, the flexible disc has been replaced by a compressible spring 8, and the distance member 5 has a different shape. Accordingly, the permanent magnet 3 is moved against a biasing force provided by the compressible spring 8, but otherwise the contaminant sensor 1 of FIGS. 2a-2c operates essentially as described above with reference to FIGS. 1a-1c.

Figure 3:
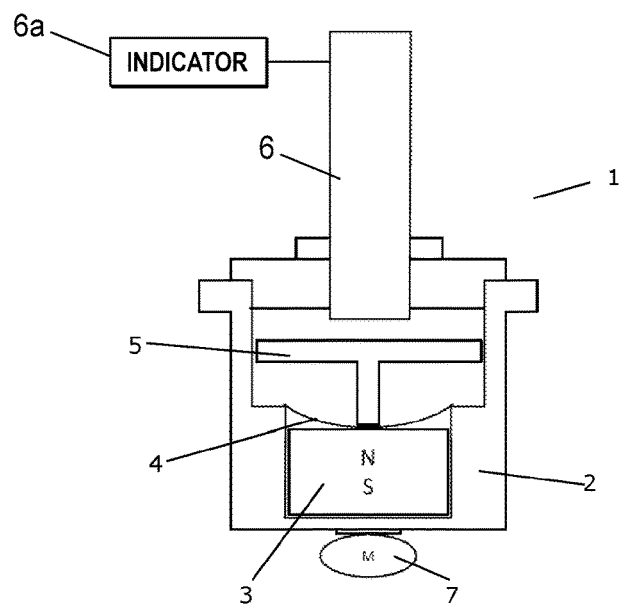
FIGS. 3-9 are cross sectional views of a contaminant sensors according to various embodiments of the invention.

FIG. 3 is a cross sectional view of a contaminant sensor 1 according to a third embodiment of the invention. The contaminant sensor 1 is shown in a fully activated state. The contaminant sensor 1 of FIG. 3 is very similar to the contaminant sensor 1 of FIGS. 1a-1c, and it will therefore not be described in detail here.

In the contaminant sensor 1 of FIG. 3 the distance element 5 is in the form of a disc mounted on a rod, which is attached to the flexible disc 4. This allows the distance sensor 6 to be arranged relatively far away from the permanent magnet 3, while the distance being measured by the distance sensor 1, i.e. the distance to the disc of the distance element 5, is relatively small.

Figure 4:
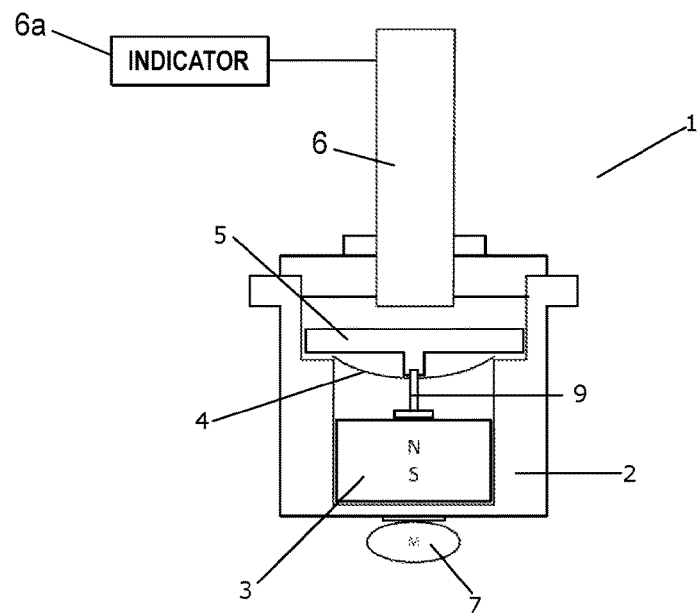

FIG. 4 is a cross sectional view of a contaminant sensor 1 according to a fourth embodiment of the invention. The contaminant sensor 1 is shown in a fully activated state. The contaminant sensor 1 of FIG. 4 is very similar to the contaminant sensor 1 of FIG. 3, and it will therefore not be described in detail here.

In the contaminant sensor 1 of FIG. 4, the flexible disc 4 is coupled to the permanent magnet 3 via an extension member 9. The extension member 9 could, e.g., be a steel wire. This allows the permanent magnet 3 to be arranged even further from the distance sensor 6, while having the flexible disc 4 arranged close to the permanent magnet 3. However, it may still be envisaged that the flexible disc 4 is arranged far away from the permanent magnet 3.

Figure 5:
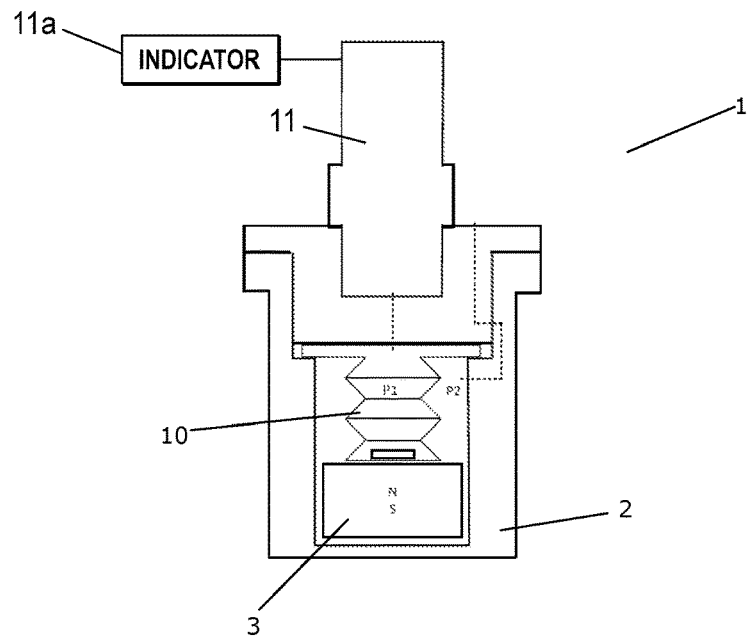

FIG. 5 is a cross sectional view of a contaminant sensor 1 according to a fifth embodiment of the invention. Similarly to the embodiments described above, the contaminant sensor 1 comprises a sensor housing 2 having a permanent magnet 3 arranged movably therein. The part of the contaminant sensor 1 where the permanent magnet 3 is positioned can be arranged in contact with a lubricant flow, and magnetizable contaminants can be collected at an outer surface of the sensor housing 2, due to the magnetic field provided by the permanent magnet 3, essentially as described above.

The permanent magnet 3 is coupled to a resilient member, in the form of a bellow 10. A sensor element, in the form of a pressure sensor 11, is arranged partly inside the sensor housing 2, in such a manner that it measures the pressure, P1, inside the bellow 10.

When the permanent magnet 3 is moved towards the contaminants collected at the outer surface of the sensor housing 2, as described above, the pressure inside the bellow 10 decreases. This change in pressure is detected by the pressure sensor 11, and provides a suitable measure for the displacement of the permanent magnet 3, due to the contaminants collected on the outer surface of the sensor housing 2. Accordingly, the measured pressure provides a suitable measure for the amount of contaminants which has been collected on the outer surface of the sensor housing 2.

Thus, when the measured pressure decreases below a predefined threshold value, an indicator 11a generates an alert signal.

According to this embodiment, the actual displacement of the permanent magnet 3 may be very small, in particular if a liquid is arranged inside the bellow 10. However, the changes in pressure inside the bellow 10, due to the small displacement of the permanent magnet 3, may be detectable.

Figure 6:
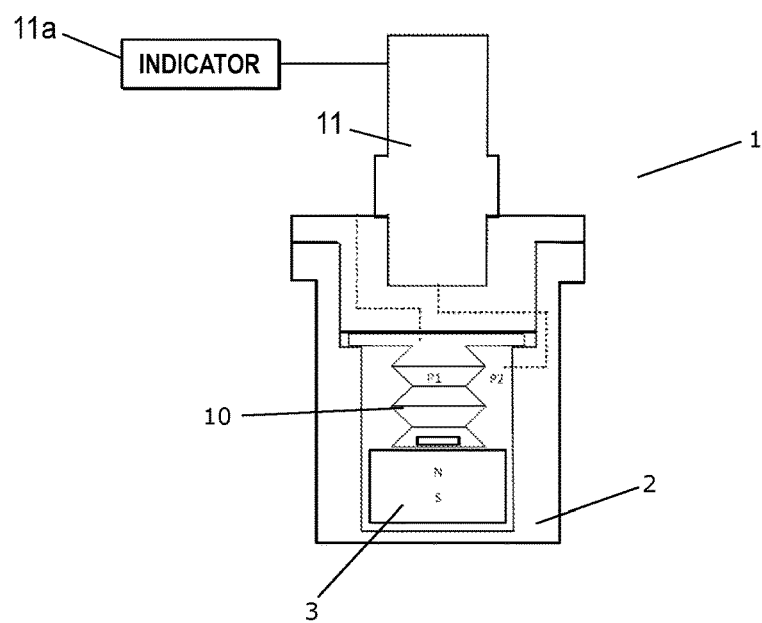

FIG. 6 is a cross sectional view of a contaminant sensor 1 according to a sixth embodiment of the invention. The contaminant sensor 1 of FIG. 6 is very similar to the contaminant sensor 1 of FIG. 5, and it will therefore not be described in detail here.

In the contaminant sensor 1 of FIG. 6, the pressure sensor 11 is arranged to measure a pressure, P2, prevailing inside a closed portion of the sensor housing 2, but outside the bellow 10. The bellow 10 is also arranged inside the closed portion of the sensor housing 2.

When the permanent magnet 3 is displaced as described above, and the pressure, P1, inside the bellow 10 thereby decreases, the pressure, P2, prevailing in the closed portion of the sensor housing increases. Thus, according to this embodiment, an indicator 11a generates an alert signal when the measured pressure, P2, increases above a predefined threshold value.

Figure 7:
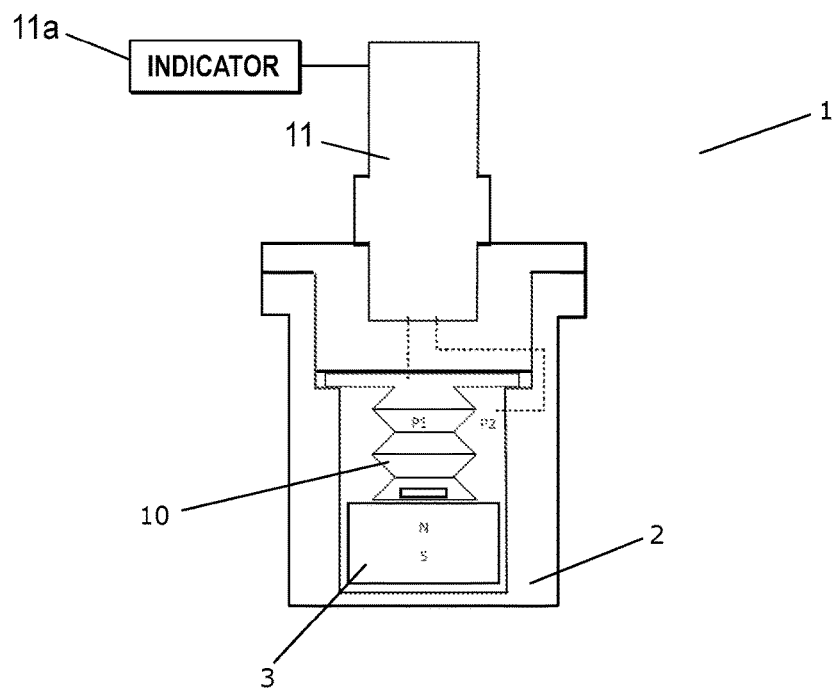

FIG. 7 is a cross sectional view of a contaminant sensor 1 according to a seventh embodiment of the invention. The contaminant sensor 1 of FIG. 7 is very similar to the contaminant sensor 1 of FIG. 5, and it will therefore not be described in detail here.

In the contaminant sensor 1 of FIG. 7, the pressure sensor 11 is arranged to measure the pressure, P1, inside the bellow 10, as well as the pressure, P2, prevailing in the closed portion of the sensor housing 2. Accordingly, a differential pressure across the wall of the bellow 10 can be obtained by means of the pressure sensor 11. This provides a more accurate measure for the displacement of the permanent magnet 3, because any effects caused by changes in the ambient pressure or ambient temperature will only influence the absolute pressures, P1 and P2, but not the differential pressure across the wall of the bellow 10.

Figure 8:
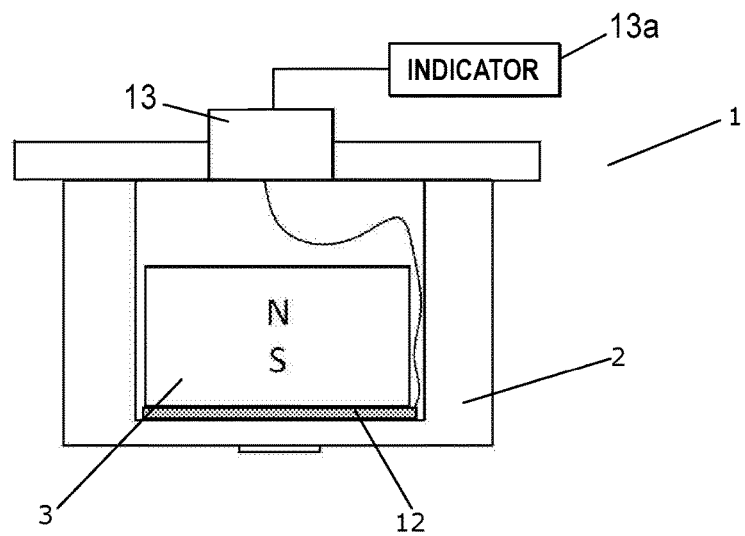

FIG. 8 is a cross sectional view of a contaminant sensor 1 according to an eighth embodiment of the invention. Similarly to the embodiments described above, the contaminant sensor 1 of FIG. 8 comprises a sensor housing 2 having a permanent magnet 3 arranged movably therein. The permanent magnet 3 is coupled to a resilient member, in the form of a deformable pad 12. When the permanent magnet 3 is moved, because it is attracted towards contaminants collected on the exterior surface of the sensor housing, the deformable pad 12 is squeezed by the permanent magnet 3, and thereby the deformable pad 12 undergoes deformation in the form of compression. The degree of deformation of the deformable pad 12 depends upon the displacement of the permanent magnet 3, and thereby on the amount of contaminants which has been collected on the outer surface of the sensor housing 2.

The deformable pad 12 is provided with sensor means (not visible), e.g. in the form of a strain gauge or a piezo resistive element embedded in or mounted on the deformable pad 12, which measures the amount of deformation of the deformable pad 12. This results in an electrical signal, which is supplied to an electronics box 13. When the electrical signal received at the electronics box 13 reaches a level which indicates that a certain amount of contaminants has been collected on the outer surface of the sensor housing 2, an indicator 13a generates an alert.

Figure 9:
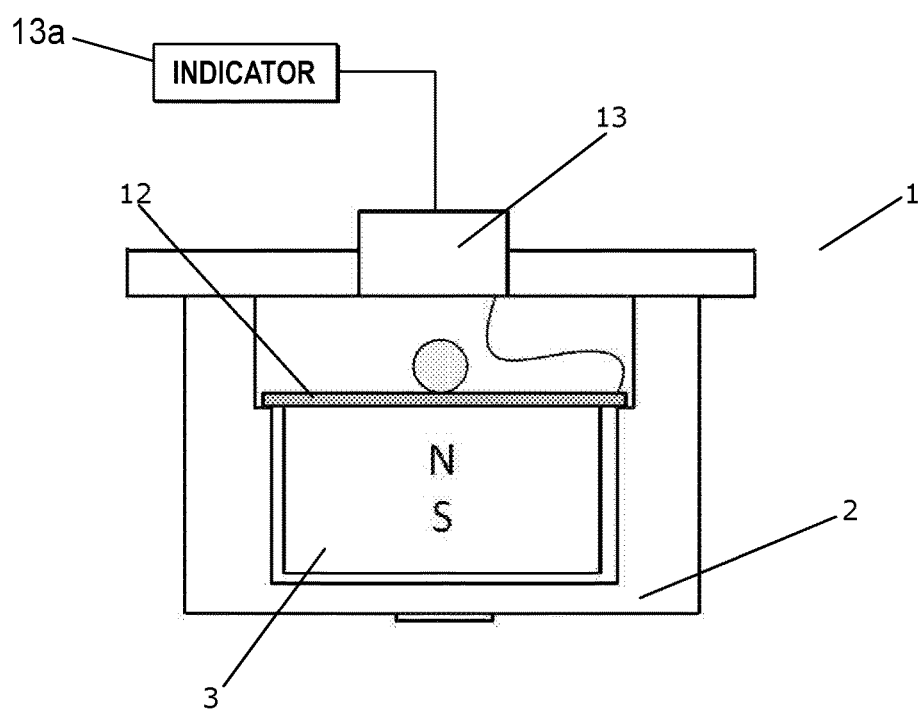

FIG. 9 is a cross sectional view of a contaminant sensor 1 according to a ninth embodiment of the invention. The contaminant sensor 1 of FIG. 9 is very similar to the contaminant sensor 1 of FIG. 8, and it will therefore not be described in detail here.

In the contaminant sensor 1 of FIG. 9, the deformable pad 12 is coupled to the permanent magnet 3 at an end which is facing away from the part of the sensor housing 2 where the contaminants are collected. Thus, when the permanent magnet 3 is moved, as contaminants are collected on the outer surface of the sensor housing 2, the deformable pad 12 is stretched, i.e. it undergoes deformation in the form of stretching. The degree of deformation is detected, essentially as described above with reference to FIG. 8.

Figure 10:
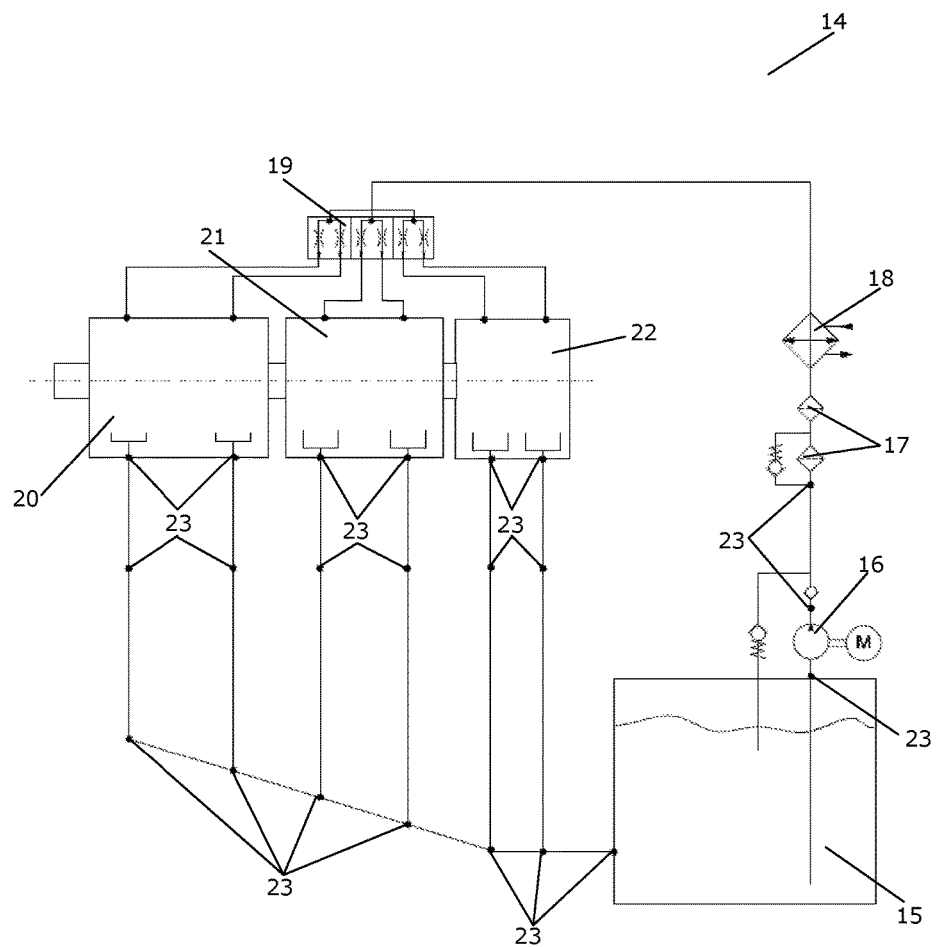
FIG. 10 is a diagrammatic view of a lubrication system according to an embodiment of the invention.

FIG. 10 is a diagrammatic view of a lubrication system 14 according to an embodiment of the invention. The lubrication system 14 is arranged for providing lubrication to a number of moving parts of a wind turbine.

The lubrication system 14 comprises a lubricant tank 15, a pump 16, a number of filters 17, a heat exchanger 18, and a distributor 19. Lubricant is pumped from the lubricant tank 15, by means of the pump 16, through the filters 17 and the heat exchanger 18 to the distributor 19. In the distributor 19 the available lubricant is distributed among a main bearing system 20, a gear system 21 and a generator 22. The main bearing system 20, the gear system 21 and the generator 22 are lubricated by means of the lubricant, and the lubricant is subsequently returned to the lubricant tank 15.

The lubrication system 14 is provided with one or more contaminant sensors, according to an embodiment of the invention, mounted in one or more of the positions 23. Thus, the presence of magnetizable contaminants in the lubricant flowing in the lubrication system 14 can be detected in the manner described above.

FIGS. 11-15 illustrate contaminant sensors 1 according an embodiment of the invention, arranged in various positions in a lubrication system. The lubrication system could, e.g., be the lubrication system 14 of FIG. 10.

Figure 11:
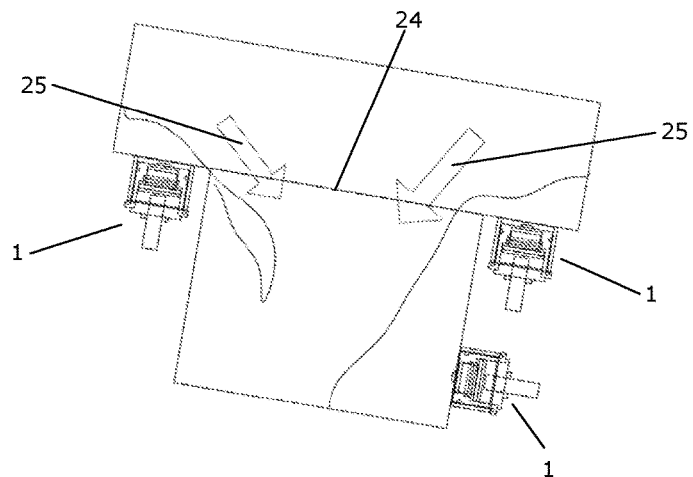
FIGS. 11-15 illustrate contaminant sensors according to an embodiment of the invention arranged at various positions in a lubrication system.

FIG. 11 illustrates three possible positions of contaminant sensors 1 near an outlet 24 from a lubricant consumer. The lubricant consumer could, e.g., be a main bearing system, a gear system or a generator of a wind turbine, as illustrated in FIG. 10.

In a wind turbine, the drive train, and thereby also the main bearing system, the gear system and the generator, are inclined slightly relative to a horizontal direction. Thereby an outlet 24 from one of these lubricant consumers is also tilted slightly relative to a horizontal direction, as illustrated in FIG. 11. Therefore the force of gravity will cause the lubricant leaving the lubricant consumer via the outlet 24 to move along the direction illustrated by arrows 25.

In order to ensure that the contaminant sensors 1 are brought into contact with the lubricant flow, and that magnetizable contaminants present in the lubricant flow are brought to a position in the vicinity of one of the contaminant sensors 1, the contaminant sensors 1 are arranged in positions where the lubricant is trapped, or where the lubricant is naturally led by means of the force of gravity.

Figure 12:
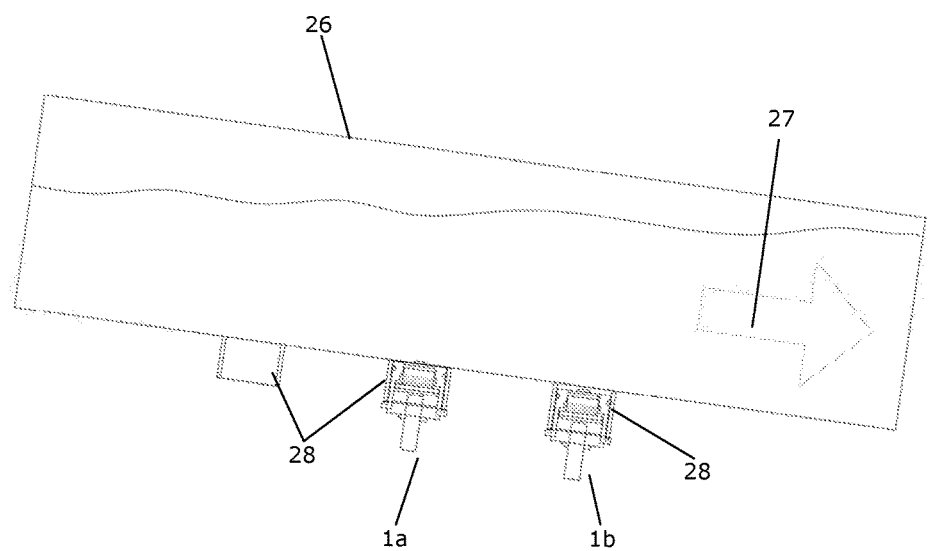

FIG. 12 illustrates another part of a lubrication system, in the form of a lubricant pipe 26 with a relatively large diameter. Due to the large diameter of the lubricant pipe 26, the lubricant flows relatively slowly through the lubricant pipe 26. Furthermore, the lubricant pipe 26 is slightly inclined relative to a horizontal direction, and therefore the lubricant moves along the direction indicated by arrow 27, due to the force of gravity.

Two contaminant sensors 1a, 1b are mounted on a lower part of the lubricant pipe 26. Thereby it is ensured that the lubricant is led past the contaminant sensors 1.

One of the contaminant sensors 1a has a sensor housing which is arranged substantially in alignment with an outer wall of the lubricant pipe 26. This provides a good contact between the contaminant sensor 1a and the lubricant flowing in the lubricant pipe 26.

The other contaminant sensor 1b has a sensor housing which is arranged at a small distance from the outer wall of the lubricant pipe 26. Thereby a small cavity is formed between the sensor housing and the interior of the lubricant pipe 26, the cavity being in open contact with the interior of the lubricant pipe 26. This has the consequence that some of the lubricant flowing in the lubricant pipe 26 is trapped in the cavity. Thereby it is ensured that magnetizable contaminants present in the lubricant which is trapped in the cavity are actually collected by the contaminant sensor 1b.

The contaminant sensors 1a, 1b are each mounted in a holder 28. This allows the contaminant sensors 1a, 1b to be removed from the lubrication system, along with any collected contaminants, e.g. in order to inspect the contaminant sensors 1a, 1b. A third holder 28 is shown, which does not have a contaminant sensor mounted therein.

Figure 13:
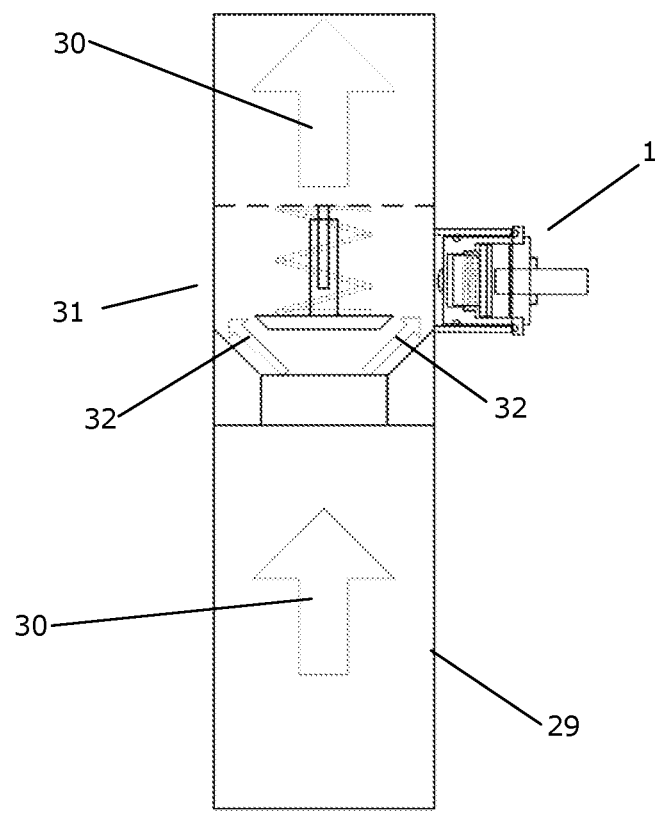

FIG. 13 illustrates yet another part of a lubrication system, in the form of a substantially vertical lubricant pipe 29. The lubricant flows through the lubricant pipe 29 along the direction indicated by the arrows 30, i.e. in an upwards direction, against the force of gravity.

A check valve 31 is arranged in the lubricant pipe 29, in order to prevent lubricant from flowing in a direction opposite to the direction indicated by the arrows 30. Lubricant passing the check valve 31 is forced towards the walls of the lubricant pipe 20, as indicated by arrows 32. A contaminant sensor 1 is mounted on the lubricant pipe 29 at a position immediately downstream with respect to the check valve 31, i.e. at a position where the lubricant is forced towards the walls of the lubricant pipe, and thereby towards the contaminant sensor 1. Thereby it is ensured that the contaminant sensor 1 is brought into contact with the lubricant flowing in the lubricant pipe 29.

Figure 14:
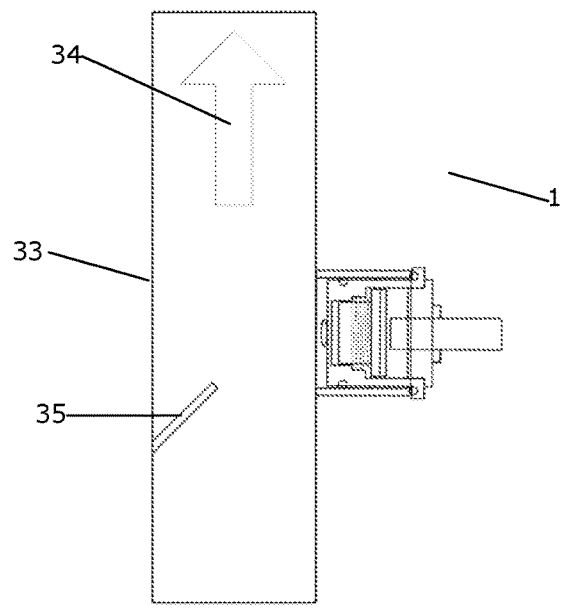

FIG. 14 illustrates yet another part of a lubrication system, also in the form of a substantially vertical lubricant pipe 33, having a relatively small diameter. Lubricant flowing through the lubricant pipe 33 flows substantially along the direction indicated by arrow 34, i.e. in a substantially upwards direction. A contaminant sensor 1 is mounted on the lubricant pipe 33.

Since the diameter of the lubricant pipe 33 is relatively small, the lubricant flows through the lubricant pipe 33 at a relatively high speed. There is therefore a risk that the lubricant, along with any contaminants contained therein, simply passes the contaminant sensor 1, and that the contaminants are thereby not collected by the contaminant sensor 1. In order to ensure that the contaminant sensor 1 is brought into contact with the lubricant, a diverter 35 is arranged inside the lubricant pipe 33, in order to direct the lubricant towards the contaminant sensor 1, and possibly slow down the lubricant flow.

Figure 15:
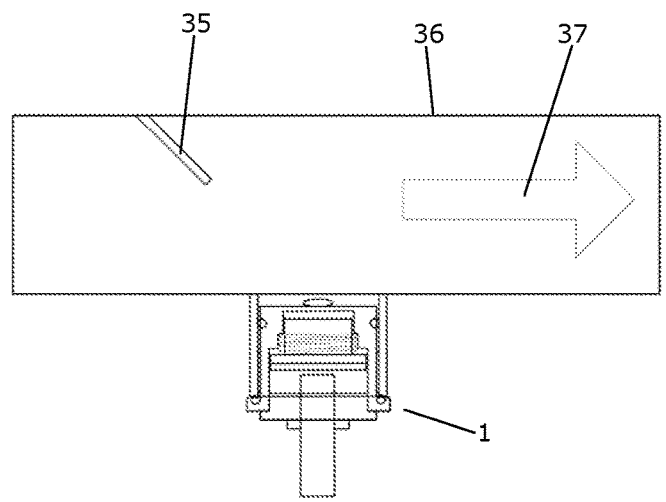

FIG. 15 illustrates yet another part of a lubrication system, in the form of a substantially horizontal lubricant pipe 36, having a relatively small diameter. Lubricant flowing through the lubricant pipe 36 flows substantially along the direction indicated by arrow 37, i.e. substantially from left to right in the Figure. A contaminant sensor 1 is mounted on a lower part of the lubricant pipe 36. Thereby the force of gravity will lead the lubricant flowing in the lubricant pipe 36 towards the contaminant sensor 1.

However, since the diameter of the lubricant pipe 36 is relatively small, the lubricant flows through the lubricant pipe 36 at a relatively high speed, and there is therefore a risk that contaminants present in the lubricant are not collected by the contaminant sensor 1, as described above, with reference to FIG. 14. Therefore a diverter 35 is arranged inside the lubricant pipe 36, in order to direct the lubricant towards the contaminant sensor 1, and possibly slow down the lubricant flow.

The invention claimed is:

1. A contaminant sensor for detecting magnetizable contaminants present in a lubricant flow, the contaminant sensor comprising:
    a sensor housing,
    a permanent magnet arranged movably inside the sensor housing,
    a resilient member operationally coupled to the permanent magnet,
    a sensor element arranged to detect a displacement of the permanent magnet inside the sensor housing, and
    an indicator arranged to generate an alert signal when a displacement and/or a rate of change of displacement of the permanent magnet inside the sensor housing exceeds a predefined threshold value,
    wherein the permanent magnet is arranged to move inside the sensor housing in response to the magnetizable contaminants collected on an outer surface of the sensor housing.

2. The contaminant sensor according to claim 1, wherein the resilient member comprises a bellow.

3. The contaminant sensor according to claim 1, wherein the sensor element is or comprises a distance sensor arranged to measure a distance between the distance sensor and the permanent magnet or a member attached to the permanent magnet.

4. The contaminant sensor according to claim 1, wherein the resilient member is or comprises a bellow attached to the permanent magnet, and wherein the sensor element is or comprises a pressure sensor arranged to measure a pressure inside and/or outside the bellow.

5. The contaminant sensor according to claim 1, wherein the sensor element is or comprises a force sensor arranged to measure a force exerted by the permanent magnet.

6. The contaminant sensor according to claim 1, wherein the permanent magnet is movable against a force provided by the resilient member in response to the magnetizable contaminants collected on the outer surface of the sensor housing.

7. The contaminant sensor according to claim 1, wherein the sensor element is at least partly arranged inside the sensor housing.

8. The contaminant sensor according to claim 1, wherein the resilient member comprises a spring element.

9. A lubrication system for lubricating a wind turbine component, the lubrication system having a contaminant sensor according to claim 1 detachably mounted therein.

10. The lubrication system according to claim 9, wherein the wind turbine component is or forms part of a drive train.

11. The lubrication system according to claim 9, wherein the contaminant sensor is arranged to retain contaminants collected on an outer surface of the sensor housing, the collected contaminants thereby being removable from the lubrication system along with the detachable contaminant sensor.

12. A wind turbine comprising a lubrication system according to claim 9.

\* \* \* \* \*